US012365785B2

(12) United States Patent
Zheng et al.

(10) Patent No.: US 12,365,785 B2
(45) Date of Patent: Jul. 22, 2025

(54) GLYCOL ETHER ARYL ESTER PLASTICIZER

(71) Applicant: Eastman Chemical Company, Kingsport, TN (US)

(72) Inventors: Pinguan Zheng, Johnson City, TN (US); Curtis Louis Schilling, III, Kingsport, TN (US); Cornelius Johannes Hermans, Heinkenszand (NL); Joseph Alexander DeLoach, Jonesborough, TN (US); Damon Ray Billodeaux, Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 585 days.

(21) Appl. No.: 17/595,250

(22) PCT Filed: Jun. 12, 2020

(86) PCT No.: PCT/US2020/037369
§ 371 (c)(1),
(2) Date: Nov. 12, 2021

(87) PCT Pub. No.: WO2020/263593
PCT Pub. Date: Dec. 30, 2020

(65) Prior Publication Data
US 2022/0227962 A1 Jul. 21, 2022

Related U.S. Application Data

(60) Provisional application No. 62/866,731, filed on Jun. 26, 2019.

(51) Int. Cl.
*C08K 5/101* (2006.01)
*C07C 69/78* (2006.01)
*C08K 5/12* (2006.01)

(52) U.S. Cl.
CPC .............. *C08K 5/101* (2013.01); *C07C 69/78* (2013.01); *C08K 5/12* (2013.01)

(58) Field of Classification Search
CPC ..................................................... C08K 5/101
See application file for complete search history.

(56) References Cited

U.S. PATENT DOCUMENTS

| | | | |
|---|---|---|---|
| 4,489,188 A | 12/1984 | Jones et al. | |
| 4,620,026 A | 10/1986 | Siegel | |
| 4,950,702 A | 8/1990 | Arendt | |
| 6,969,735 B1 | 11/2005 | Godwin | |
| 7,208,545 B1 | 4/2007 | Brunner et al. | |
| 7,973,194 B1 | 7/2011 | Kinkade et al. | |
| 9,403,965 B2 | 8/2016 | Laufer et al. | |
| 2008/0058450 A1 | 3/2008 | Stimpson et al. | |
| 2012/0181056 A1 | 7/2012 | Chaudhary et al. | |
| 2013/0062094 A1 | 3/2013 | Naert et al. | |
| 2015/0112008 A1 | 4/2015 | Patiul et al. | |
| 2016/0096350 A1 | 4/2016 | Lu | |
| 2016/0159051 A1 | 6/2016 | Lu et al. | |
| 2016/0159057 A1 | 6/2016 | Butler | |
| 2016/0160005 A1 | 6/2016 | Lu et al. | |
| 2016/0160030 A1 | 6/2016 | Chen et al. | |
| 2018/0105673 A1* | 4/2018 | Schilling, III | ........... C08K 5/12 |
| 2019/0359789 A1 | 11/2019 | Pfeiffer et al. | |
| 2022/0185989 A1 | 6/2022 | DeLoach, III et al. | |
| 2022/0325068 A1 | 10/2022 | DeLoach et al. | |

FOREIGN PATENT DOCUMENTS

| | | | |
|---|---|---|---|
| EP | 3 333 219 A1 | 6/2018 | |
| EP | 3 473 669 A1 | 4/2019 | |
| EP | 3 476 890 A1 | 5/2019 | |
| JP | H0350246 A | 3/1991 | |
| JP | 05339413 A | * | 12/1993 |
| JP | H05339413 A | 12/1993 | |
| JP | 11 302445 A | 11/1999 | |
| RU | 2015/156846 A | 7/2017 | |
| RU | 2 633 963 C2 | 10/2017 | |
| WO | WO 2007/021987 A1 | 2/2007 | |
| WO | WO 2009/085453 A2 | 7/2009 | |
| WO | WO 2016094203 | 6/2016 | |

OTHER PUBLICATIONS

English machine translation of Asaumi et al. (JP 5-339413) (Year: 1993).*
Notification of Transmittal of the International Search Report and the Written Opinion of the International Searching Authority with Date of Mailing of Oct. 9, 2020 received in International Application No. PCT/US2020/037373.
Notification of Transmittal of the International Search Report and the Written Opinion of the International Searching Authority with Date of Mailing of Oct. 9, 2020 received in International Application No. PCT/US2020/037375.
Notification of Transmittal of the International Search Report and the Written Opinion of the International Searching Authority with Date of Mailing of Oct. 9, 2020 received in International Application No. PCT/US2020/037361.
Notification of Transmittal of the International Search Report and the Written Opinion of the International Searching Authority with Date of Mailing of Oct. 9, 2020 received in International Application No. PCT/US2020/037365.
Tan Jihuai et al: "Highly efficient and recyclable catalysts SnC12-Xh3pw12040/ac With Bronsted and Lewis acid sites for terephthalic acid esterification", Journal of the Taiwan Institute of Chemical Engineers, Elsevier, Amsterdam, NL; vol. 86, Mar. 31, 2018, pp. 18-24, Mar. 31, 2018.

(Continued)

*Primary Examiner* — Michael F Pepitone
(74) *Attorney, Agent, or Firm* — Tammye L. Taylor Polk; Pan Yuan

(57) ABSTRACT

Disclosed is the use of glycol ether aryl ester plasticizers as viscosity reducing agents in plastisols comprising di(2-ethylhexyl) terephthalate, 1,2-cyclohexane dicarboxylic acid diisononyl ester, or diisononyl phthalate as the primary plasticizer. The glycol ether aryl ester plasticizers improve viscosity and viscosity stability while maintaining or improving plastisol properties such as Shore A Hardness and fusion time.

17 Claims, No Drawings

(56) References Cited

OTHER PUBLICATIONS

Malik Sameena N et al: "Treatment of pharmaceutical industrial wastewater by nano-catalyzed ozonation in a semi-batch reactor for improved biodegradability", Science of the Total Environment vol. 678; Apr. 17, 2019; pp. 114-122.
Conn, R. C., et al.; "Some Aromatic Esters of the Monoalkyl Ethers of Ethylene Glycol and Diethylene Glycol"; Journal of the American Chemical Society, 54(11), 1932, pp. 4370-4372.
Ram, A. and Schneider, Z; "Flow Properties of PVC Plastisols"; Industrial & Engineering Chemistry Product Research and Development, 9(3); Sep. 1, 1970; pp. 286-291.
Sears, J. K. and Darby, J. R.; "The Technology of Plasticizers" 1982; pp. 104-107.
Co-pending U.S. Appl. No. 17/595,253, filed Nov. 12, 2021; Zhenpeng Li et al.
Co-pending U.S. Appl. No. 17/595,327, filed Nov. 15, 2021; Joseph Alexander DeLoach and Curtis Louis Schilling, III; now U. S. Publication No. 2022-0185989.
Co-pending U.S. Appl. No. 17/594,972, filed Nov. 4, 2021; Xhenpeng Li and Eric Jon Moskala.
Co-pending U.S. Appl. No. 17/594,969, filed Nov. 4, 2021; Joseph Alexander DeLoach et al.
Notification of Transmittal of the International Search Report and the Written Opinion of the International Searching Authority with Date of Mailing of Oct. 9, 2020 received in International Application No. PCT/US2020/037369.
Non-Final Office Communication received in U.S. Appl. No. 17/595,327 dated Jun. 3, 2024.

* cited by examiner

GLYCOL ETHER ARYL ESTER PLASTICIZER

FIELD OF THE INVENTION

This invention pertains to plastisols with lower initial viscosity and improved viscosity stability. Specifically, the invention pertains to the use of glycol ether aryl esters as a second plasticizer to improve the viscosity aspects of plastisols using general-purpose plasticizers while maintaining or improving processing and/or final product properties.

BACKGROUND OF THE INVENTION

Various "specialty plasticizers" and other formulation additives have been proposed and utilized for improving plasticizer performance. Many of these additives suffer from high volatility, which is of increasing concern for air quality and workplace exposure. For example, diluents such as mineral spirits can effectively reduce the viscosity of a PVC plastisol. However, mineral spirits is a quite volatile mixture of hydrocarbons with complete evaporation occurring by 220° C., much lower than the boiling point of commercial ester plasticizers. In addition, the hydrocarbons contribute little or nothing to plasticization of PVC. Some plasticizers, such as lower phthalates and dibenzoates, have good plasticizing efficiency and can increase the rate of fusion with PVC plastisols. These plasticizers, however, cause an increase in plastisol viscosity and a tendency for the plastisol viscosity to increase over time. Dibenzoate and lower phthalate plasticizers can also reduce the time for a plasticized PVC powder blend to become free flowing, but the lower phthalates have come under scrutiny for health and toxicity concerns, leading to their regulation or ban in some jurisdictions and/or applications. Alkyl monobenzoates, for example 2-ethylhexyl benzoate, isononyl benzoate, and isodecyl benzoate, have been developed to fill these performance gaps, but these also have deficiencies. These monoesters, with 15, 16 and 17 carbons, respectively, still have significant volatile content which present a risk to formulators such as flooring producers who supply into sensitive markets. Furthermore, these alkyl monobenzoates are not highly efficient plasticizers in two widely used measures, reduction of Shore A hardness and increase in fusion rates. These deficiencies provide an opportunity for improved plastisols, such as those in this invention.

The objective of this invention is to provide novel formulations of plasticized polyvinyl chloride (PVC) which have unexpected benefits in processing and properties. One objective is to provide plasticizers which, when formulated with polyvinyl chloride (PVC) and optionally with other plasticizers, improve the processing of PVC formulations. Another objective is to provide plasticizers which enable PVC plastisols to have low viscosities which do not increase excessively upon aging, and wherein the plasticizers do not contribute emissions of volatile organic compounds (VOC's) in the PVC formulation. These emissions include those within the "semi-volatile" or s-VOC range according to standard emission testing protocols. Another objective is to provide plasticizers which have improved plasticizing efficiency compared to alkyl monobenzoates. Another objective is to provide plasticizers which increase the rate of fusion of PVC formulations. Another objective is to provide plasticizers which reduce the time required for a PVC powder/plasticizer blend to dry. In each instance, the inventive plasticizers may be used alone, or in combination with other plasticizers. The other plasticizers are most typically "general-purpose" plasticizers, which deliver a reasonable balance of performance and economics. The general-purpose plasticizers often benefit from improvements that specialized plasticizers, such as the subject ones of this invention, provide.

SUMMARY OF THE INVENTION

The present application discloses a plasticizer composition comprising:
(a) a general-purpose plasticizer; and
(b) a plasticizer of formula I:

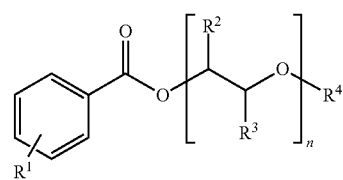

wherein:
  $R^1$ is hydrogen or methyl;
  $R^2$ and $R^3$ are independently hydrogen or methyl, with the proviso that $R^2$ and $R^3$ are not each methyl;
  $R^4$ is unbranched or branched $(C_{1-10})$alkyl or phenyl; and
  n is an integer from 1 to 8;
wherein the plasticizer of formula I is present in the plasticizer composition from about 10 wt. % to about 50 wt. % based on the total weight of the plasticizer composition.

The present application also discloses a plastisol comprising
(a) a resin;
(b) a general-purpose plasticizer; and
(c) a plasticizer of formula I:

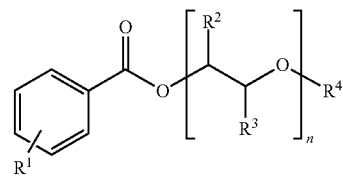

wherein:
  $R^1$ is hydrogen or methyl;
  $R^2$ and $R^3$ are independently hydrogen or methyl, with the proviso that $R^2$ and $R^3$ are not each methyl;
  $R^4$ is unbranched or branched $(C_{1-10})$alkyl or phenyl; and
  n is an integer from 1 to 8;
wherein the plastisol comprises 30 to 200 parts plasticizer component per 100 parts resin, wherein the plasticizer component comprises the general purpose plasticizer and the plasticizer of formula I; and wherein the plasticizer component comprises 10 wt. % to 50 wt. % of the plasticizer of formula I.

The present application also discloses a compound selected from the group consisting of 2-hexyloxyethyl benzoate, 2-(2-propoxyethoxy)ethyl benzoate, 2-(2-(2-propoxyethoxy)ethoxy)ethyl benzoate, 2-propoxy-1-propyl benzoate, 2-butoxy-1-propyl benzoate, and 1-butoxy-2-propyl benzoate.

DETAILED DESCRIPTION

Definitions

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons" or "($C_{1-5}$) hydrocarbons", is intended to specifically include and disclose $C_1$ and $C_5$ hydrocarbons as well as $C_2$, $C_3$, and $C_4$ hydrocarbons. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

"Alkyl" groups suitable for use herein can be straight, branched, or cyclic, and can be saturated or unsaturated. Alkyl groups suitable for use herein include any ($C_{1-20}$), ($C_{1-12}$), ($C_{1-5}$), or ($C_{1-3}$) alkyl groups. In various embodiments, the alkyl can be a $C_{1-5}$ straight chain alkyl group. In still other embodiments, the alkyl can be a $C_{1-3}$ straight chain alkyl group. Specific examples of suitable alkyl groups include, but are not limited to, methyl, ethyl, n-propyl, isopropyl, n-butyl, isobutyl, sec-butyl, tert-butyl, pentyl, hexyl, octyl, decyl, dodecyl, cyclopentyl, and cyclohexyl groups. Examples such as propyl, butyl, decyl, and the like are not limited to the normal forms, they also include the branched forms. For example, propyl includes n-propyl and isopropyl.

"Alkoxy" is an alkyl attached to an oxygen (e.g., alkyl-O—).

One embodiment of the application discloses is a plastisol comprising a resin, a first plasticizer and a second plasticizer. The resin is not particularly limited and can be any resin typically used in plastisols. In one aspect, the resin comprises polyvinyl chloride, polyvinyl acetate, acrylic polymers, and/or vinyl chloride-containing copolymers. In one aspect, the resin comprises polyvinyl chloride. In one aspect, the resin comprises polyvinyl chloride and acrylic polymer. In one aspect, the resin comprises polyvinyl chloride and polyvinyl acetate. In one aspect, the resin comprises polyvinyl chloride and vinyl chloride-containing copolymers comprising acetate. In one aspect, the resin comprises polyvinyl chloride and vinyl chloride-containing copolymers comprising acrylic.

Plastisols typically include "general-purpose" plasticizers which deliver a reasonable balance of performance and economics. Three common general-purpose plasticizers are di(2-ethylhexyl) terephthalate, 1,2-cyclohexane dicarboxylic acid diisononyl ester, and diisononyl phthalate. In one aspect, the first plasticizer is di(2-ethylhexyl) terephthalate. Di(2-ethylhexyl) terephthalate is also known as DEHT and DOTP. In one aspect, the first plasticizer is 1,2-cyclohexane dicarboxylic acid diisononyl ester (DINCH). In one aspect, the first plasticizer is diisononyl phthalate (DINP).

Plasticizer Composition

The present application discloses a plasticizer composition comprising:
(a) a general-purpose plasticizer; and (b) a plasticizer of formula I:

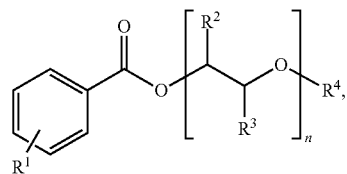

wherein: $R^1$ is hydrogen or methyl; $R^2$ and $R^3$ are independently hydrogen or methyl, with the proviso that $R^2$ and $R^3$ are not each methyl; $R^4$ is unbranched or branched ($C_{1-10}$)alkyl or phenyl; and n is an integer from 1 to 8;

wherein the plasticizer of formula I is present in the plasticizer composition from about 10 wt. % to about 50 wt. % based on the total weight of the plasticizer composition.

In one embodiment, $R^1$ is hydrogen. In one embodiment, $R^1$ is methyl.

In one embodiment, $R^2$ is hydrogen, and $R^3$ is methyl. In one embodiment, $R^2$ is methyl, and $R^3$ is hydrogen. In one embodiment, $R^2$ is hydrogen, and $R^3$ is hydrogen.

In one embodiment, $R^4$ is an unbranched or branched ($C_{1-10}$)alkyl. In one class of this embodiment, $R^4$ is methyl, ethyl, unbranched or branched propyl, unbranched or branched butyl, unbranched or branched pentyl, unbranched or branched hexyl, unbranched or branched heptyl, unbranched or branched octyl, unbranched or branched nonyl, or unbranched or branched decyl. In one class of this embodiment, $R^4$ is methyl. In one class of this embodiment, $R^4$ is ethyl. In one class of this embodiment, $R^4$ is an unbranched or branched propyl. In one class of this embodiment, $R^4$ is unbranched or branched butyl. In one class of this embodiment, $R^4$ is unbranched or branched pentyl. In one class of this embodiment, $R^4$ is unbranched or branched hexyl. In one class of this embodiment, $R^4$ is unbranched or branched heptyl. In one class of this embodiment, $R^4$ is unbranched or branched octyl. In one subclass of this class, $R^4$ is 2-ethylhexyl. In one class of this embodiment, $R^4$ is unbranched or branched nonyl. In one class of this embodiment, $R^4$ is unbranched or branched decyl.

In one embodiment, $R^4$ is phenyl.

In one embodiment, $R^4$ is methyl, ethyl, unbranched or branched propyl, unbranched or branched butyl, unbranched or branched hexyl, unbranched or branched octyl, or phenyl. In one class of this embodiment, $R^4$ is unbranched or branched propyl or unbranched or branched butyl.

In one embodiment, n is 1 to 7. In one embodiment, n is 1 to 6. In one embodiment, n is 1 to 5. In one embodiment, n is 1 to 4. In one embodiment, n is 1 to 3. In one embodiment, n is 1 to 2. In one embodiment, n is 1. In one embodiment, n is 2. In one embodiment, n is 3. In one embodiment, n is 4. In one embodiment, n is 5. In one embodiment, n is 6. In one embodiment, n is 7. In one embodiment, n is 8.

In one embodiment, the plasticizer of formula I is 2-methoxyethyl benzoate, 2-ethoxyethyl benzoate, 2-propoxyethyl benzoate, 2-butoxyethyl benzoate, 2-hexyloxyethyl benzoate, 2-(2-ethylhexyloxy)ethyl benzoate, 2-phenoxyethyl benzoate, 2-(2-methoxyethoxy)ethyl benzoate, 2-(2-ethoxyethoxy)ethyl benzoate, 2-(2-propoxyethoxy)ethyl benzoate, 2-(2-butoxyethoxy)ethyl benzoate, 2-(2-hexyloxyethoxy)ethyl benzoate, 2-(2-(2-ethylhexyloxy)ethoxy)ethyl benzoate, 2-(2-phenoxyethoxy)ethyl benzoate, 2-(2-(2-methoxyethoxy)ethoxy)ethyl benzoate, 2-(2-(2-ethoxyethoxy)ethoxy)ethyl benzoate, 2-(2-(2-propoxyethoxy)ethoxy)ethyl benzoate, 2-(2-(2-butoxyethoxy)ethoxy)ethyl benzoate, 2-(2-(2-hexyloxyethoxy)ethoxy)ethyl benzoate, 2-(2-(2-ethylhexyloxy)ethoxy)ethoxy)ethyl benzoate, 2-(2-(2-phenoxyethoxy)ethoxy)ethyl benzoate, 1-methoxy-2-propyl benzoate, 1-ethoxy-2-propyl benzoate, 1-propoxy-2-propyl benzoate, 1-butoxy-2-propyl benzoate, 1-phenoxy-2-propyl benzoate, 2-methoxy-1-propyl benzoate, 2-ethoxy-1-propyl benzoate, 2-propoxy-1-propyl benzoate, 2-butoxy-1-propyl benzoate, 2-phenoxy-1-propyl benzoate, isomers of dipropylene glycol monomethyl ether benzoate, isomers of dipropylene glycol monoethyl ether benzoate, isomers of dipropylene glycol monopropyl ether benzoate, isomers of dipropylene glycol monobutyl ether benzoate, isomers of tripropylene glycol monomethyl ether benzoate, isomers of tripropylene glycol monoethyl ether benzoate, isomers of tripropylene glycol monopropyl ether benzoate, or isomers of tripropylene glycol monobutyl ether benzoate.

In one class of this embodiment, the general-purpose plasticizer is a terephthalate ester plasticizer, a phthalate ester plasticizer, a cyclohexane-1,2-dicarboxylat ester plasticizer, a cyclohexane-1,4-dicarboxylate ester plasticizer, an alkyl sulfonate plasticizer, a pentaerythritol ester plasticizer, or a citrate ester plasticizer. In one class of this embodiment, the general-purpose plasticizer is a terephthalate ester plasticizer, a phthalate ester plasticizer, or a cyclohexane-1,2-dicarboxylate ester plasticizer.

In one class of this embodiment, the benzoate plasticizer I is 2-butoxyethyl benzoate, 2-propoxyethyl benzoate, 2-(2-methoxyethoxy)ethyl benzoate, 2-(2-propoxyethoxy)ethyl benzoate, 2-(2-butoxyethoxy)ethyl benzoate, 2-(2-ethoxyethoxy)ethyl benzoate, or 2-(2-(2-butoxyethoxy)ethoxy)ethyl benzoate.

In one subclass of this class, the general-purpose plasticizer is a terephthalate ester plasticizer, a phthalate ester plasticizer, a cyclohexane-1,2-dicarboxylate ester plasticizer, a cyclohexane-1,4-dicarboxylate ester plasticizer, an alkyl sulfonate plasticizer, a pentaerythritol ester plasticizer, or a citrate ester plasticizer. In one subclass of this class, the general-purpose plasticizer is a terephthalate ester plasticizer, a phthalate ester plasticizer, or a cyclohexane-1,2-dicarboxylate ester plasticizer.

In one embodiment, the general-purpose plasticizer is a terephthalate ester plasticizer, a phthalate ester plasticizer, or a cyclohexane-1,2-dicarboxylate ester plasticizer.

In one class of this embodiment, the general-purpose plasticizer is a terephthalate ester plasticizer, a phthalate ester plasticizer, a cyclohexane-1,2-dicarboxylate ester plasticizer, a cyclohexane-1,4-dicarboxylate ester plasticizer an alkyl sulfonate plasticizer, a pentaerythritol ester plasticizer, or a citrate ester plasticizer.

In one subclass of this class, the general purpose plasticizer is bis(2-ethylhexyl)terephthalate, bis(isononyl) cyclohexane-1,2-dicarboxylate, or bis(isononyl) phthalate.

In one embodiment, the plasticizer composition further comprises: (c) a fast-fusing plasticizer. In one class of this embodiment, the fast-fusing plasticizer comprises: (i) a dibenzoate plasticizer, or (ii) a plasticizer of formula

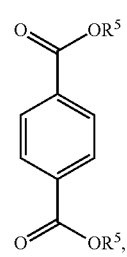

II wherein each $R^5$ is independently an unbranched or branched $(C_{1-9})$alkyl or —O—$CH_2$—$CH_2$—O—$(C_{1-9})$alkyl.

In one class of this embodiment, each $R^5$ is independently chosen from methyl, ethyl, unbranched or branched propyl, unbranched or branched butyl, unbranched or branched pentyl, unbranched branched hexyl, 2-methoxyethanoxy, 2-ethoxyethoxy, 2-propoxylethoxy, 2-butoxyethoxy, 2-pentoxyethoxy, or 2-hexyloxyethoxy.

In one class of this embodiment, the dibenzoate plasticizer comprises oxybis(ethane-2,1-diyl) dibenzoate, (ethane-1,2-diylbis(oxy))bis(ethane-2,1-diyl) dibenzoate, polyethylene glycol dibenzoate, propane-1,3-diyldibenzoate, oxybis(propane-3,1-diyl) dibenzoate, (propane-1,3-diylbis(oxy))bis(propane-3,1-diyl) dibenzoate, 2,2,4-trimethyl-1,3-pentanediol dibenzoate, or combinations thereof.

The plasticizer of formula I is a glycol ether aryl ester. Techniques for the esterification of glycol ethers, including with aromatic carboxylic acids or their equivalents, are well known. An early example is described by Conn, Collett and Lazzell in *Journal of the American Chemical Society* 1932, 54(11), pp. 4370-4372. The reaction can be conducted by the reaction of an aryl acyl halide, aryl acyl ester, or aryl carboxylic acid with a monoalcohol of an ethylene glycol (Scheme 1).

Scheme 1.

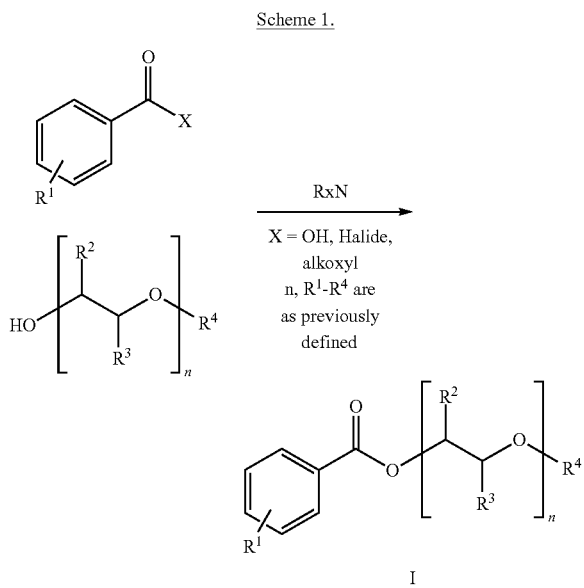

Plastisol

The present application discloses a plastisol comprising: (a) a resin; (b) a general-purpose plasticizer; and (c) a plasticizer of formula I:

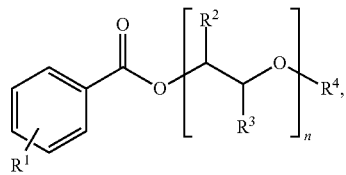

wherein: $R^1$ is hydrogen or methyl; $R^2$ and $R^3$ are independently hydrogen or methyl, with the proviso that $R^2$; and $R^3$ are not each methyl; $R^4$ is unbranched or branched $(C_{1-10})$alkyl or phenyl; and n is an integer from 1 to 8; wherein the plastisol comprises 30 to 200 parts plasticizer component per 100 parts resin, wherein the plasticizer component comprises the general purpose plasticizer and the plasticizer of formula I; and wherein the plasticizer component comprises 10 wt. % to 50 wt. % of the plasticizer of formula I. The plasticizer component is the sum total of all plasticizers in the plastisol.

In one embodiment, $R^1$ is hydrogen. In one embodiment, $R^1$ is methyl.

In one embodiment, $R^2$ is hydrogen, and $R^3$ is methyl. In one embodiment, $R^2$ is methyl, and $R^3$ is hydrogen. In one embodiment, $R^2$ is hydrogen, and $R^3$ is hydrogen.

In one embodiment, $R^4$ is an unbranched or branched $(C_{1-10})$alkyl. In one class of this embodiment, $R^4$ is methyl, ethyl, unbranched or branched propyl, unbranched or branched butyl, unbranched or branched pentyl, unbranched or branched hexyl, unbranched or branched heptyl, unbranched or branched octyl, unbranched or branched nonyl, or unbranched or branched decyl. In one class of this embodiment, $R^4$ is methyl. In one class of this embodiment, $R^4$ is ethyl. In one class of this embodiment, $R^4$ is an unbranched or branched propyl. In one class of this embodiment, $R^4$ is unbranched or branched butyl. In one class of this embodiment, $R^4$ is unbranched or branched pentyl. In one class of this embodiment, $R^4$ is unbranched or branched hexyl. In one class of this embodiment, $R^4$ is unbranched or branched heptyl. In one class of this embodiment, $R^4$ is unbranched or branched octyl. In one subclass of this class, $R^4$ is 2-ethylyhexyl. In one class of this embodiment, $R^4$ is unbranched or branched nonyl. In one class of this embodiment, $R^4$ is unbranched or branched decyl.

In one embodiment, $R^4$ is phenyl.

In one embodiment, $R^4$ is methyl, ethyl, unbranched or branched propyl, unbranched or branched butyl, unbranched or branched hexyl, unbranched or branched octyl, or phenyl. In one class of this embodiment, $R^4$ is unbranched or branched propyl or unbranched or branched butyl. In one embodiment, n is an integer from 1 to 7. In one embodiment, n is an integer from 1 to 6. In one embodiment, n is an integer from 1 to 5. In one embodiment, n is an integer from 1 to 4. In one embodiment, n is an integer from 1 to 3. In one embodiment, n is an integer from 1 to 2. In one embodiment, n is 1. In one embodiment, n is 2. In one embodiment, n is 3. In one embodiment, n is 4. In one embodiment, n is 5. In one embodiment, n is 6. In one embodiment, n is 7. In one embodiment, n is 8.

In one embodiment, the plasticizer of formula I is 2-methoxyethyl benzoate, 2-ethoxyethyl benzoate, 2-propoxyethyl benzoate, 2-butoxyethyl benzoate, 2-hexyloxyethyl benzoate, 2-(2-ethylhexyloxy)ethyl benzoate, 2-phenoxyethyl benzoate, 2-(2-methoxyethoxy)ethyl benzoate, 2-(2-ethoxyethoxy)ethyl benzoate, 2-(2-propoxyethoxy) ethyl benzoate, 2-(2-butoxyethoxy)ethyl benzoate, 2-(2-hexyloxyethoxy)ethyl benzoate, 2-(2-(2-ethylhexyloxy) ethoxy)ethyl benzoate, 2-(2-phenoxyethoxy)ethyl benzoate, 2-(2-(2-methoxyethoxy)ethoxy)ethyl benzoate, 2-(2-(2-ethoxyethoxy)ethoxy)ethyl benzoate, 2-(2-(2-propoxyethoxy)ethoxy)ethyl benzoate, 2-(2-(2-butoxyethoxy)ethoxy)ethyl benzoate, 2-(2-(2-hexyloxyethoxy)ethoxy) ethyl benzoate, 2-(2-(2-(2-ethylhexyloxy)ethoxy)ethoxy) ethyl benzoate, 2-(2-(2-phenoxyethoxy)ethoxy)ethyl benzoate, 1-methoxy-2-propyl benzoate, 1-ethoxy-2-propyl benzoate, 1-propoxy-2-propyl benzoate, 1-butoxy-2-propyl benzoate, 1-phenoxy-2-propyl benzoate, 2-methoxy-1-propyl benzoate, 2-ethoxy-1-propyl benzoate, 2-propoxy-1-propyl benzoate, 2-butoxy-1-propyl benzoate, 2-phenoxy-1-propyl benzoate, isomers of dipropylene glycol monomethyl ether benzoate, isomers of dipropylene glycol monoethyl ether benzoate, isomers of dipropylene glycol monopropyl ether benzoate, isomers of dipropylene glycol monobutyl ether benzoate, isomers of tripropylene glycol monomethyl ether benzoate, isomers of tripropylene glycol monoethyl ether benzoate, isomers of tripropylene glycol monopropyl ether benzoate, or isomers of tripropylene glycol monobutyl ether benzoate.

In one class of this embodiment, the plasticizer of formula I is 2-butoxyethyl benzoate, 2-propoxyethyl benzoate, 2-(2-methoxyethoxy)ethyl benzoate, 2-(2-propoxyethoxy)ethyl benzoate, 2-(2-butoxyethoxy)ethyl benzoate, 2-(2-ethoxyethoxy)ethyl benzoate, or 2-(2-(2-butoxyethoxy)ethoxy) ethyl benzoate.

In one embodiment, the general-purpose plasticizer is a terephthalate ester plasticizer, a phthalate ester plasticizer, or a cyclohexane-1,2-dicarboxylate ester plasticizer.

In one class of this embodiment, the general-purpose plasticizer is a terephthalate ester plasticizer, a phthalate ester plasticizer, a cyclohexane-1,2-dicarboxylate ester plasticizer, a cyclohexane-1,4-dicarboxylate ester plasticizer an alkyl sulfonate plasticizer, a pentaerythritol ester plasticizer, or a citrate ester plasticizer.

In one subclass of this class, the general purpose plasticizer is bis(2-ethylhexyl)terephthalate, bis(isononyl) cyclohexane-1,2-dicarboxylate, or bis(isononyl) phthalate.

In one embodiment, the resin comprises polyvinyl chloride, polyvinyl acetate, acrylic polymers, and/or vinyl chloride-containing copolymers. In one class of this embodiment, the resin comprises polyvinyl chloride.

In one embodiment, the plastisol further comprises: (c) a fast-fusing plasticizer. In one class of this embodiment, the fast-fusing plasticizer comprises: (i) a dibenzoate plasticizer, or (ii) a plasticizer of formula II:

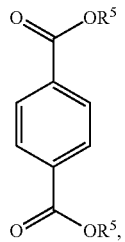

wherein each $R^5$ is independently an unbranched or branched $(C_{1-9})$alkyl or $-O-CH_2-CH_2-O-(C_{1-9})$ alkyl.

In one class of this embodiment, wherein each $R^5$ is independently chosen from methyl, ethyl, unbranched or branched propyl, unbranched or branched butyl, unbranched or branched pentyl, unbranched branched hexyl, 2-methoxyethanoxy, 2-ethoxyethoxy, 2-propoxylethoxy, 2-butoxyethoxy, 2-pentoxyethoxy, or 2-hexyloxyethoxy.

In one class of this embodiment, the dibenzoate plasticizer comprises oxybis(ethane-2,1-diyl) dibenzoate, (ethane-1,2-diylbis(oxy))bis(ethane-2,1-diyl) dibenzoate, polyethylene glycol dibenzoate, propane-1,3-diyldibenzoate, oxybis(propane-3,1-diyl) dibenzoate, (propane-1,3-diylbis(oxy))bis(propane-3,1-diyl) dibenzoate, 2,2,4-trimethyl-1,3-pentanediol dibenzoate, or combinations thereof.

In one embodiment, the plastisol comprises 30 to 200 parts plasticizer component per 100 parts resin. In one class of this embodiment, the plasticizer component comprises 10 wt. % to 50 wt. % of the plasticizer of formula I. In one class of this embodiment, the plasticizer component comprises 10 wt. % to 40 wt. % of the plasticizer of formula I. In one class of this embodiment, the plasticizer component comprises 10 wt. % to 30 wt. % of the plasticizer of formula I.

In one embodiment, the plastisol comprises 30 to 150 parts plasticizer component per 100 parts resin. In one class of this embodiment, the plasticizer component comprises 10 wt. % to 50 wt. % of the plasticizer of formula I. In one class of this embodiment, the plasticizer component comprises 10 wt. % to 40 wt. % of the plasticizer of formula I. In one class of this embodiment, the plasticizer component comprises 10 wt. % to 30 wt. % of the plasticizer of formula I.

In one embodiment, the plastisol comprises 30 to 100 parts plasticizer component per 100 parts resin. In one class of this embodiment, the plasticizer component comprises 10 wt. % to 50 wt. % of the plasticizer of formula I. In one class of this embodiment, the plasticizer component comprises 10 wt. % to 40 wt. % of the plasticizer of formula I. In one class of this embodiment, the plasticizer component comprises 10 wt. % to 30 wt. % of the plasticizer of formula I.

In one embodiment, the plastisol comprises 40 to 150 parts plasticizer component per 100 parts resin. In one class of this embodiment, the plasticizer component comprises 10 wt. % to 50 wt. % of the plasticizer of formula I. In one class of this embodiment, the plasticizer component comprises 10 wt. % to 40 wt. % of the plasticizer of formula I. In one class of this embodiment, the plasticizer component comprises 10 wt. % to 30 wt. % of the plasticizer of formula I.

One skilled in the art recognizes that the amount of the plasticizer of formula I used is a balance between its cost relative to the general-purpose plasticizer and the performance it imparts to the plastisol.

In one embodiment, the plastisol comprises other components, the other components comprise fillers, pigments, stabilizers, foaming agents, hollow materials, elastomeric materials, rheology control additives, and/or adhesion promoters. In one class of this embodiment, the fillers comprise calcium carbonate and/or fly ash. In one subclass of this class, the stabilizers comprise metal soaps, epoxidized oils, epoxidized fatty acid esters, and/or organotin compounds.

In one embodiment, the plastisol comprises 10 to 300 parts other components per 100 parts resin. In one class of this embodiment, the other components comprise fillers, pigments, stabilizers, foaming agents, hollow materials, elastomeric materials, rheology control additives, and/or adhesion promoters. In one subclass of this class, the fillers comprise calcium carbonate and/or fly ash. In one subclass of this class, the stabilizers comprise metal soaps, epoxidized oils, epoxidized fatty acid esters, and/or organotin compounds.

In one embodiment, the plastisol comprises 10 to 150 parts other components per 100 parts resin. In one class of this embodiment, the other components comprise fillers, pigments, stabilizers, foaming agents, hollow materials, elastomeric materials, rheology control additives, and/or adhesion promoters. In one subclass of this class, the fillers comprise calcium carbonate and/or fly ash. In one subclass of this class, the stabilizers comprise metal soaps, epoxidized oils, epoxidized fatty acid esters, and/or organotin compounds.

In one embodiment, the plastisol comprises 25 to 125 parts other components per 100 parts resin. In one class of this embodiment, the other components comprise fillers, pigments, stabilizers, foaming agents, hollow materials, elastomeric materials, rheology control additives, and/or adhesion promoters. In one subclass of this class, the fillers comprise calcium carbonate and/or fly ash. In one subclass of this class, the stabilizers comprise metal soaps, epoxidized oils, epoxidized fatty acid esters, and/or organotin compounds.

In one embodiment, the plastisol can be formulated or produced in a manner which incorporates more free volume into the fused plastisol. In one such technique, mechanical frothing may be applied to produce a foamed plastisol.

In one embodiment, a chemical foaming agent is used in the plastisol which results in a foamed structure after fusing is completed. One non-limiting example of such a foaming agent is azodicarbonamide. In one class of this embodiment, a catalyst is used along with the chemical foaming agent. In one subclass of this class, foam stabilizers are used in the plastisol. In one class of this embodiment, foam stabilizers are used in the plastisol.

In one embodiment, hollow materials are incorporated into the plastisol. Non-limiting examples of hollow materials include glass beads, microbeads, and/or microspheres, which can be produced from either inorganic or polymeric organic substances. In one class of this embodiment, the hollow materials are thermoplastic microspheres.

In one embodiment, the plastisol comprises elastomeric materials. Non-limiting examples of elastomeric materials include nitrile-butadiene rubber, natural rubber, isoprene rubber, butadiene rubber, styrene-butadiene rubber, butyl rubber, ethylene-propylene-diene monomer (EPDM) rubber, chloroprene rubber, styrenated block copolymers, ethylene-vinyl acetate copolymers, olefinic elastomers, olefinic copolymer elastomers, silicone elastomers, polysulfide elastomers, and/or polyurethane elastomers.

In one embodiment, additives to control rheology can be incorporated into the plastisols. These may include additional plasticizers or diluents. Examples of such additives include petroleum distillates; hydrocarbon oils such as, for example, mineral oil and mineral spirits; fatty acid esters; polyphenyl oligomers, optionally partially hydrogenated; and organic solvents. Conversely, thickeners may be added to boost viscosity as desired. Several materials and techniques for adjusting plastisol rheology are well known in the art.

In one embodiment, the plastisol comprises adhesion promoters. Non-limiting examples of adhesion promoters include polyamidoamines, blocked isocyanates and isocyanurates, silanes, and/or epoxy resins.

One skilled in the art knows that plastisols are readily made by contacting (e.g., mixing) the ingredients until well dispersed. Plastisols may be dearated after the mixing step.

The plastisol can be formed into a fused sheet for use in emission testing. In one embodiment, the fused sheet formed from the plastisol has a total semi-volatile organic compound emissions (TSVOC) of less than 0.1 mg/m$^3$ using toluene equivalents after 28 days using the AgBB methodologies. Other non-limiting examples of emission amounts after 28 days include TSVOC of less than 0.05 mg/m$^3$, and less than 0.01 mg/m$^3$. The fused sheet consists of the plastisol when no other ingredients have been added to impact plastisol properties such as viscosity. The fused sheet consists of the plastisol is not intended to exclude normal processing aids used in the production of a fused sheet from a plastisol.

Emissions values are based on testing according to the German AgBB (Committee for Health-Related Evaluation of Building Products) methodology, February 2015 regulations.

Benzoate Plasticizers

The present application discloses a compound selected from the group consisting of 2-hexyloxyethyl benzoate, 2-(2-propoxyethoxy)ethyl benzoate, 2-(2-(2-propoxyethoxy)ethoxy)ethyl benzoate, 2-propoxy-1-propyl benzoate, 2-butoxy-1-propyl benzoate, and 1-butoxy-2-propyl benzoate.

EXAMPLES

Abbreviations

Ex is example(s); Comp is comparative; Comp Ex is comparative example(s); min is minute(s); mol is mole(s); g is gram(s); mL is milliliter(s); ° C. is degree(s) Celsius; aq is aqueous; mmHg is millimeter(s) mercury; sec is second(s); rpm is revolutions per minute; psi is pounds per square inch; ° F. is degree(s) Fahrenheit; PVC is poly(vinyl chloride); phr is parts per hundred resin; cP is centipoise; m is meter(s); µm is micrometer; DOTP is bis(2-ethylhexyl) terephthalate (sold as Eastman™ 168 Non-Phthalate Plasticizer); DBT is Dibutyl terephthalate (sold as Eastman Effusion™ Plasticizer);

Ex 1—Synthesis of 2-Butoxyethyl Benzoate

A 1-liter round bottomed flask was equipped with a Dean-Stark trap, nitrogen inlet, temperature probe, and reflux condenser. To the flask was charged 2-butoxy ethanol (130 g, 1.10 mol), benzoic acid (148 g, 1.21 mol), titanium tetraisopropoxide (3.13 g, 0.011 mol), and toluene (100 mL). The reaction mixture was heated to 130–190° C. with continuous removal of water for 5 h. After the mixture was cooled to 80° C., 10% aq NaOH (200 mL) was added, and the resulting mixture was stirred at 80° C. (30 min). The crude material was cooled and filtered through a pad of diatomaceous earth. The filtrate was washed successively with 10% aq NaOH, water, and brine solution. Crude product was purified using a Vigreux column (125-131° C., 1.6-2.2 mmHg) to give the title compound.

Ex 2-10 and Comp Ex C1-C6

Using the procedure for the synthesis of Ex 1 with the appropriate alcohol, Ex 2-10 were prepared (See Table 1). Isofol 12, 16, 20, and 24 branched alcohols were obtained from Sasol Chemicals North America; the number represents the number of carbons in the alcohol. Neodol 23 alcohol, a blend of mostly linear C12 and C13 alcohols, was obtained from Shell Chemical LP. Isotridecyl alcohol was obtained from KH Neochem Americas Inc.

Comp Ex C7. Synthesis of 2-(2-(2-Ethylhexyloxy)ethoxy)ethyl 2-ethylhexanoate

A 1-liter round bottomed flask was equipped with a Dean-Stark trap, nitrogen inlet, temperature probe, and reflux condenser. To the flask was charged 2-(2-(2-ethylhexyl)oxy)ethoxy ethanol (200 g, 0.916 mol), 2-ethylhexanoic acid (139 g, 0.962 mol), titanium tetraisopropoxide (1.30 g, 0.0045 mol), and toluene (35 mL). Crude product was purified using a 10-tray Oldershaw column under full vacuum (147-153° C., 0.8-1.8 mmHg, 30% take-off ratio) to give the title compound.

The procedure for the synthesis of Comp Ex C7 was adapted to synthesize the benzoate esters given in Table 1.

TABLE 1

Synthesis of Ex 1-10 and Comp Ex C1-C9.

| Ex # | Starting Alcohol | Structure/Name |
|---|---|---|
| 1 | 2-butoxyethan-1-ol | 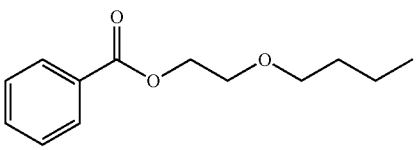<br>2-butoxyethyl benzoate |

TABLE 1-continued

Synthesis of Ex 1-10 and Comp Ex C1-C9.

| Ex # | Starting Alcohol | Structure/Name |
|---|---|---|
| 2 | 2-propoxyethan-1-ol | 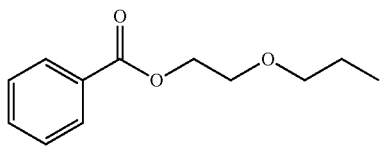<br>2-propoxyethyl benzoate |
| 3 | 2-(2-methoxyethoxy)ethan-1-ol | 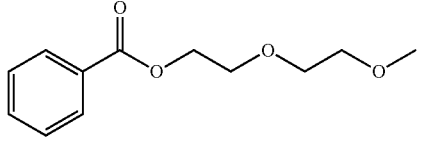<br>2-(2-methoxyethoxy)ethyl benzoate |
| 4[1] | 2-(2-propoxyethoxy)ethan-1-ol | 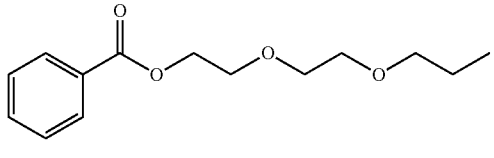<br>2-(2-propoxyethoxy)ethyl benzoate |
| 5 | 2-(2-butoxyethoxy)ethan-1-ol | 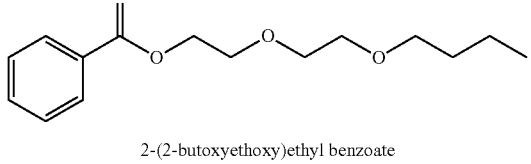<br>2-(2-butoxyethoxy)ethyl benzoate |
| 6 | 2-(2-ethoxyethoxy)ethan-1-ol | 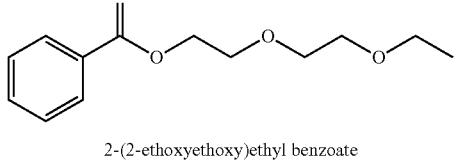<br>2-(2-ethoxyethoxy)ethyl benzoate |
| 7 | 2-(2-(2-butoxyethoxy)ethoxy)ethan-1-ol | 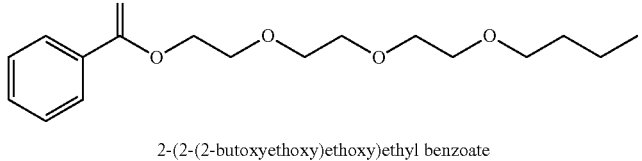<br>2-(2-(2-butoxyethoxy)ethoxy)ethyl benzoate |
| 8 | 2-(2-ethylhexyloxy)ethan-1-ol | 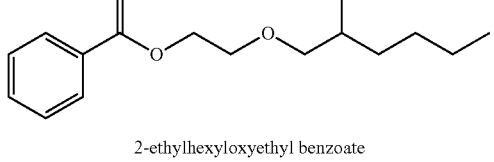<br>2-ethylhexyloxyethyl benzoate |
| 9 | 2-(2-(2-ethylhexyloxy)ethoxy)ethan-1-ol | 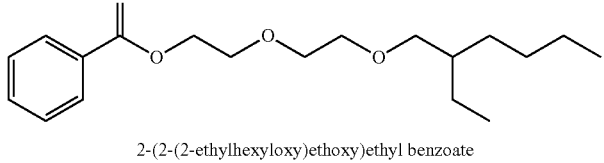<br>2-(2-(2-ethylhexyloxy)ethoxy)ethyl benzoate |

TABLE 1-continued

Synthesis of Ex 1-10 and Comp Ex C1-C9.

| Ex # | Starting Alcohol | Structure/Name |
|---|---|---|
| 10 | 2-(2-(2-(2-ethylhexyloxy)ethoxy)ethoxy)ethan-1-ol | 2-(2-(2-(2-ethylhexyloxy)ethoxy)ethoxy)ethyl benzoate |
| C1 | Isofol 24 | Isofol 24 benzoate |
| C2 | Isofol 20 | Isofol 20 benzoate |
| C3 | Isofol 16 | Isofol 16 benzoate |
| C4 | Isofol 12 | Isofol 12 benzoate |
| C5 | Neodol 23 | Neodol 23 benzoate |

TABLE 1-continued

Synthesis of Ex 1-10 and Comp Ex C1-C9.

| Ex # | Starting Alcohol | Structure/Name |
|---|---|---|
| C6 | Isotridecyl alcohol | Isotridecyl benzoate |
| C7 | 2-(2-ethylhexyloxy)ethanol | 2-ethylhexyloxyethyl 2-ethylhexanoate |
| C8 | 2-(2-(2-ethylhexyl)oxy)ethoxy ethanol | 2-(2-(2-ethylhexyloxy)ethoxy)ethyl 2-ethylhexanoate |
| C9 | 2-(2-ethylhexyloxy)ethanol and 2-(2-(2-ethylhexyl)oxy)ethoxy ethanol | Mixture of 2-ethylhexyloxyethyl 2-ethylhexanoate and 2-(2-(2-ethylhexyloxy)ethoxy)ethyl 2-ethylhexanoate |

[1] Verified by mass spectrometry: M + 252

Viscosity Additives VA1-VA6—Commercially Available

Viscosity Additive VA1 is isodecyl benzoate, commercially available from ExxonMobil Corporation as JAYFLEX MB10. Viscosity Additive VA2 is triethylene glycol di-2-ethylhexanoate, commercially available from Eastman Chemical Company as EASTMAN TEG-EH. Viscosity Additive VA3 is 2,2,4-trimethyl-1,3-pentanediol diisobutyrate, commercially available from Eastman Chemical Company as Eastman TXIB formulation additive. Viscosity Additive VA4 does not contain an additional plasticizer other than DOTP, commercially available from Eastman Chemical Company as EASTMAN 168 Non-Phthalate Plasticizer. Viscosity Additive VA5 is di-2-ethylhexyl adipate, commercially available from Eastman Chemical Company as Eastman DOATM plasticizer. Viscosity Additive VA6 is HB-40 Process Fluid, commercially available from Eastman Chemical Company. Each of these viscosity additive materials was obtained from the commercial sources and used without further purification.

In addition to the plasticizers described as Ex 1-10, Comp Ex C1-C9 and commercially available Viscosity Additives VA1-VA6, the ingredients described in Table 2 were used in the formulations and test results described below. The term "phr" refers to the addition level in weight of the ingredient per 100 parts weight of the PVC resin. Each ingredient was obtained from the commercial sources and was used without further purification.

TABLE 2

Ingredients and additives used in PVC formulations

| Material | Description | Supplier |
|---|---|---|
| Geon 121A | PVC paste resin, K-74 | Mexichem S.A.B. de C.V. |
| DOTP | Bis(2-ethylhexyl) terephthalate | Eastman Chemical Company |
| DBT | Dibutyl terephthalate | Eastman Chemical Company |
| Benzoflex ™ 2088 Plasticizer | Blend of diethylene, triethylene, and dipropylene glycol dibenzoates | Eastman Chemical Company |
| Drapexe ® 6.8 | Epoxidized soybean oil | Galata Chemicals |
| AKCROSTAB LT-4798 | Barium/zinc stabilizer | Akcros Chemicals Inc. |

General Procedure for the Preparation of PVC Plastisols

A FlackTek SpeedMixer™ model 600 FVZ was used to prepare PVC plastisols. The liquid additives were charged into a mixing cup and premixed until homogeneous. Then, the PVC resin was added, stirred to distribute with the liquid additives, and the cup was placed into the mixer. The contents were shaken in the mixer for 30 sec at 1200 rpm and the side of the container was scraped, then the contents were shaken in the mixer for 40 sec at 1600 rpm and the side of the container was scraped again. This process was repeated if necessary to insure complete dispersion. The resulting plastisol was then deaerated in a desiccator to which vacuum was applied for 20 min.

EVALUATION OF PLASTISOLS

Brookfield Viscosities

Brookfield viscosities were determined using a Brookfield DV-1 digital viscometer, in accordance with ASTM Method D1824, "Standard Test Method for Apparent Viscosity of Plastisols and Organosols at Low Shear Rates." Spindle speeds of 2 rpm and 20 rpm were used in the evaluations.

Severs Viscosities

Severs viscosities were determined using a Burrell-Severs Model A120 Rheometer, in accordance with ASTM Method D1823, "Standard Test Method for Apparent Viscosity of Plastisols and Organosols at High Shear Rates by Extrusion Viscometer." Nitrogen pressures of 40 psi and 80 psi were used in the evaluations.

Fusion Determination

Fusion data were generated using a Brabender Intelli-Torque Plasti-Corder® rheometer, in accordance with ASTM Method D2538, "Standard Practice for Fusion of Poly(Vinyl Chloride) (PVC) Compounds Using a Torque Rheometer." Fusion times are reported as the time at which the peak mixer torque is recorded.

Shore A Hardness

Shore A hardness measurements were performed in accordance with ASTM Method D2240, "Standard Test Method for Rubber Property—Durometer Hardness." Specimens were prepared by fusing plastisols produced as described above at 375° F. for 30 min. Results reported are average readings from five specimens, rounded to the nearest whole number.

Dry Times

Dry times were measured in accordance with ASTM Method D2396, "Standard Test Methods for Powder-Mix Time of PVC Resins Using a Torque Rheometer." OxyVinyls® 240F PVC resin (OxyVinyls, LP), K-value 70, along with 18 phr Burgess 30P clay (Burgess Pigment Company) and 5 phr epoxidized soybean oil (Drapex® 6.8, Galata Chemicals) were used. Mixtures of 60 phr DOTP and 10 phr of the plasticizers in the Examples and Comparative Examples, and commercially available viscosity control additives were used in the dry time determinations, except that Comp Ex 13 used 70 phr DOTP only.

Ex 11-14 and Comp Ex C10—Plasticizer Performance

An experiment was conducted to assess the relative performance of relatively low molecular weight glycol ether benzoates against isodecyl benzoate as plastisol viscosity control additives. These plastisol formulations csisted of 100 phr Geon 121A PVC resin, 3 phr epoxidized soybean oil, 3 pr AKCROSTAB LT 4798 stabilizer, 45 phr DOTP, and 15 phr of the viscosity control additive. The viscosity control additive used for each example is identified in Tables 3-5 by the Example number or Comparative Example number for those produced and by the VA# above for those purchased. The PVC resin, epoxidized oil, AKCROSTAB LT 4798, DOTP, and viscosity control additive levels were used in all subsequent plastisol formulations. Brookfield Viscosities were measured at 2 rpm and 20 rpm. Severs viscosities were measured at 40 psi and 80 psi. Both viscosity measurements were performed on the day the plastisol was made (initial) and then again at first, third, and seventh days after production and are listed in Tables 3 and 4, respectively. Fusion time for each plastisol and Shore A hardness were measured and are listed in Table 5.

TABLE 3

Plastisol Brookfield viscosity for Ex 11-14 and Comp Ex C10.

| Ex | Viscosity Additive | rpm | Initial | Day 1 | Day 3 | Day 7 |
|----|----|----|----|----|----|----|
| | | | | Viscosity (cP) | | |
| 11 | 1 | 2 | 1500 | 1800 | 2540 | 2700 |
| 12 | 2 | 2 | 1440 | 1640 | 1800 | 2020 |
| 13 | 3 | 2 | 2100 | 2300 | 2920 | 3700 |
| 14 | 4 | 2 | 1660 | 1800 | 1960 | 2180 |
| C10 | VA1 | 2 | 1900 | 2180 | 2560 | 2980 |
| 11 | 1 | 20 | 1375 | 1555 | 1990 | 2270 |
| 12 | 2 | 20 | 1325 | 1445 | 1610 | 1860 |
| 13 | 3 | 20 | 1825 | 2115 | 2505 | 3055 |
| 14 | 4 | 20 | 1560 | 1705 | 1855 | 2020 |
| C10 | VA1 | 20 | 1835 | 2155 | 2460 | 2620 |

TABLE 4

Plastisol Severs viscosity-Ex 11-14 and Comp Ex C10.

| Ex | Viscosity Additive | Psi | Initial | Day 1 | Day 3 | Day 7 |
|----|----|----|----|----|----|----|
| | | | | Viscosity (cP) | | |
| 11 | 1 | 40 | 5212 | 5067 | 5513 | 5638 |
| 12 | 2 | 40 | 5197 | 5060 | 5354 | 5443 |
| 13 | 3 | 40 | 6736 | 6615 | 8082 | 9119 |
| 14 | 4 | 40 | 6427 | 6393 | 6461 | 6449 |
| C10 | VA1 | 40 | 13569 | 12106 | 11338 | 10934 |
| 11 | 1 | 80 | 6166 | 6015 | 6334 | 6631 |
| 12 | 2 | 80 | 6338 | 6308 | 6673 | 6932 |
| 13 | 3 | 80 | 8182 | 8637 | 10386 | 12160 |
| 14 | 4 | 80 | 7921 | 7708 | 7941 | 8124 |
| C10 | VA1 | 80 | 15628 | 14302 | 13490 | 12793 |

The viscosity data illustrate superior plastisol viscosity reduction and control for plastisols comprising the glycol ether benzoates, particularly those with propyl or butyl ether groups (Ex 1, 2, and 4), compared to isodecyl benzoate, Comp Ex 10. Ex 11, 12 and 14 have lower Brookfield and Severs viscosity values at each measurement time compared to Comp Ex C10. Ex 13 has lower Severs viscosity values at each measurement time compared to Ex C10.

TABLE 5

Fusion Time and Shore A Hardness for Ex 11-14 and Comp Ex C10.

| Ex | Viscosity Additive | Fusion Time (Min) | Shore A Hardness |
|----|----|----|----|
| 11 | 1 | 17.70 | 66 |
| 12 | 2 | 17.57 | 69 |
| 13 | 3 | 16.13 | 65 |
| 14 | 4 | 17.93 | 67 |
| C10 | VA1 | 18.47 | 70 |

Each of the plastisols comprising glycol ether benzoates, Ex 11-14, showed faster fusion times than the plastisol comprising isodecyl benzoate, Comp Ex C10. Reduced fusion time can enable faster production rates and lower energy use for manufacturers of articles from PVC plastisols. The glycol ether benzoates of Ex 1-4 are more efficient plasticizers than isodecyl benzoate as shown by the lower Shore A Hardness values for Ex 11-14 plastisols (66-69) as compared to the Shore A Hardness value of Comp Ex C10 (70). Higher efficiency means that less plasticizer can be used to attain desired product properties, often resulting in cost savings to the manufacturer.

Ex 15 and Comp Ex C11-C14—Plasticizer Performance

An experiment was conducted to assess the relative performance of another glycol ether benzoate, 2-(2-butoxyethoxy)ethyl benzoate (Ex 5), against isodecyl benzoate and other non-oxygenated alkyl monobenzoates as plastisol viscosity control additives. These plastisol formulations consisted of 100 phr Geon 121A PVC resin, 3 phr epoxidized soybean oil, 3 phr AKCROSTAB LT 4798 stabilizer, 45 phr DOTP, and 15 phr of the viscosity control additive. The viscosity control additive used for each example is identified in Tables 6-8 by the Example number or Comparative Example number for those produced and by the VA# above for those purchased. The PVC resin, epoxidized soybean oil, AKCROSTAB LT 4798, DOTP, and viscosity control additive levels were used in all subsequent plastisol formulations. Brookfield Viscosities were measured at 2 rpm and 20 rpm. Severs viscosities were measured at 40 psi and 80 psi. Both viscosity measurements were performed on the day the plastisol was made (initial) and then again at first, third, and seventh days after production and are listed in Table 6 and 7, respectively. Fusion time for each plastisol and Shore A hardness were measured and are listed in Table 8.

TABLE 6

Plastisol Brookfield viscosity for Ex 15 and Comp Ex C11-C14.

| Ex | Viscosity Additive | rpm | Initial | Day 1 | Day 3 | Day 7 |
|---|---|---|---|---|---|---|
| | | | | Viscosity (cP) | | |
| 15 | 5 | 2 | 2220 | 2420 | 2600 | 2680 |
| C11 | C1 | 2 | 2600 | 2460 | 2420 | 2340 |
| C12 | C2 | 2 | 2480 | 2560 | 2380 | 2340 |
| C13 | C3 | 2 | 2420 | 2400 | 2400 | 2360 |
| C14 | VA1 | 2 | 2200 | 2340 | 2500 | 2460 |
| 15 | 5 | 20 | 1870 | 2090 | 2220 | 2230 |
| C11 | C1 | 20 | 2810 | 2840 | 2770 | 2710 |
| C12 | C2 | 20 | 2320 | 2430 | 2450 | 2450 |
| C13 | C3 | 20 | 2180 | 2300 | 2320 | 2310 |
| C14 | VA1 | 20 | 1770 | 2030 | 2250 | 2190 |

TABLE 7

Plastisol Severs viscosity for Ex 15 and Comp Ex C11-C14.

| Ex | Viscosity Additive | psi | Initial | Day 1 | Day 3 | Day 7 |
|---|---|---|---|---|---|---|
| | | | | Viscosity (cP) | | |
| 15 | 5 | 40 | 5979 | 5822 | 5985 | 5961 |
| C11 | C1 | 40 | 24754 | 25804 | 25614 | 24500 |
| C12 | C2 | 40 | 19218 | 20228 | 19673 | 18988 |
| C13 | C3 | 40 | 17358 | 17477 | 16692 | 16857 |
| C14 | VA1 | 40 | 11930 | 11116 | 9910 | 9473 |
| 15 | 5 | 80 | 7294 | 7178 | 7393 | 7529 |
| C11 | C1 | 80 | 25938 | 26289 | 27357 | 26346 |
| C12 | C2 | 80 | 21122 | 21621 | 21208 | 20418 |
| C13 | C3 | 80 | 19342 | 19526 | 18959 | 18016 |
| C14 | VA1 | 80 | 14047 | 12933 | 11348 | 10983 |

The Brookfield viscosity data show comparable performance between 2-(2-butoxyethoxy)ethyl benzoate and the non-oxygenated alkyl monobenzoates, as the Brookfield viscosities of Ex 15 and Comp Ex C11-C14 are similar. The higher shear, Severs viscosity data, however, show clear advantages for the glycol ether benzoate. The Plastisol of Ex 15 has a Severs viscosity from below 6000 cP at 40 psi and below 7600 cP at 80 psi whereas Comp Ex C11-C14 range from over 9400 cP to almost 26000 cP at 40 psi and above 10900 cP to almost 27400 cP at 80 psi. The Severs viscosity stability is an important indicator of performance in high shear processes such as knife coating.

TABLE 8

Fusion Time and Shore A Hardness for Ex 15 and Comp Ex C11-C14.

| Ex | Viscosity Additive | Fusion Time (Min) | Shore A Hardness |
|---|---|---|---|
| 15 | 5 | 17.33 | 69 |
| C11 | C1 | 22.57 | 85 |
| C12 | C2 | 20.67 | 74 |
| C13 | C3 | 19.73 | 77 |
| C14 | VA1 | 18.27 | 71 |

The plastisol comprising glycol ether benzoates, Ex 15, showed faster fusion time (17.3 min) than the plastisols comprising non-oxygenated alkyl monobenzoates and isodecyl benzoate, Comp Ex C11-C14, ranging from 18.3 to 22.6 min. Reduced fusion time can enable faster production rates and lower energy use for manufacturers of articles from PVC plastisols. The glycol ether benzoate of Ex 5 is a more efficient plasticizer than non-oxygenated alkyl monobenzoates and isodecyl benzoate as shown by the lower Shore A Hardness values for Ex 15 plastisol (69) as compared to the Shore A Hardness values of Comp Ex C11-C14 (71-85). Higher efficiency means that less plasticizer can be used to attain desired product properties, often resulting in cost savings to the manufacturer.

Ex 16-17 and Comp Ex C15-C17—Plasticizer Performance

An experiment was conducted to assess the relative performance of two other glycol ether benzoates, 2-(2-ethoxyethoxy)ethyl benzoate (Ex 6) and 2-(2-(2-butoxyethoxy)ethoxy)ethyl benzoate (Ex 7), against isodecyl benzoate and other non-oxygenated alkyl monobenzoates as plastisol viscosity control additives. These plastisol formulations consisted of 100 phr Geon 121A PVC resin, 3 phr epoxidized soybean oil, 3 phr AKCROSTAB LT 4798 stabilizer, 45 phr DOTP, and 15 phr of the viscosity control additive. The viscosity control additive used for each example is identified in Tables 9-11 by the Example number or Comparative Example number for those produced and by the VA# above for those purchased. The PVC resin, epoxidized soybean oil, AKCROSTAB LT 4798, DOTP, and viscosity control additive levels are used in all subsequent plastisol formulations. Brookfield Viscosities were measured at 2 rpm and 20 rpm. Severs viscosities were measured at 40 psi and 80 psi. Both viscosity measurements were performed on the day the plastisol was made (initial) and then again at first and seventh days after production and are listed in Table 9 and 10, respectively. Fusion time for each plastisol and Shore A hardness were measured and are listed in Table 11.

TABLE 9

Plastisol Brookfield viscosity for Ex 16-17 and Comp Ex C15-C17.

| Ex | Viscosity Additive | Rpm | Initial | Day 1 | Day 7 |
|---|---|---|---|---|---|
| | | | Viscosity (cP) | | |
| 16 | 6 | 2 | 2380 | 2660 | 2800 |
| 17 | 7 | 2 | 2400 | 2700 | 2860 |
| C15 | C4 | 2 | 2340 | 2440 | 2400 |

TABLE 9-continued

Plastisol Brookfield viscosity for
Ex 16-17 and Comp Ex C15-C17.

| Ex | Viscosity Additive | Rpm | Initial | Day 1 | Day 7 |
|---|---|---|---|---|---|
| | | | Viscosity (cP) | | |
| C16 | C5 | 2 | 2060 | 2260 | 2140 |
| C17 | VA1 | 2 | 2220 | 2400 | 2620 |
| 16 | 6 | 20 | 1870 | 2030 | 2370 |
| 17 | 7 | 20 | 2000 | 2240 | 2340 |
| C15 | C4 | 20 | 2050 | 2180 | 2170 |
| C16 | C5 | 20 | 1820 | 1910 | 2000 |
| C17 | VA1 | 20 | 1980 | 2090 | 2200 |

TABLE 10

Plastisol Severs viscosity for
Ex 16-17 and Comp Ex C15-C17.

| Ex | Viscosity Additive | psi | Initial | Day 1 | Day 7 |
|---|---|---|---|---|---|
| | | | Viscosity (cP) | | |
| 16 | 6 | 40 | 5181 | 5501 | 6265 |
| 17 | 7 | 40 | 7040 | 6947 | 6960 |
| C15 | C4 | 40 | 14160 | 13832 | 12297 |
| C16 | C5 | 40 | 11638 | 11225 | 9966 |
| C17 | VA1 | 40 | 12042 | 11096 | 9241 |
| 16 | 6 | 80 | 6484 | 6838 | 7974 |
| 17 | 7 | 80 | 8645 | 8602 | 8704 |
| C15 | C4 | 80 | 16616 | 15970 | 13784 |
| C16 | C5 | 80 | 13280 | 12916 | 11073 |
| C17 | VA1 | 80 | 14031 | 12694 | 10768 |

The Brookfield viscosity data show comparable performance between the glycol ether benzoates and the non-oxygenated alkyl monobenzoates, as the Brookfield viscosities of Ex 16 and 17 and Comp Ex C15-C17 are similar.

The higher shear, Severs viscosity data, however, show clear advantages for the glycol ether benzoates. The Plastisol of Ex 16 and 17 have a Severs viscosity from 5181 to 7040 cP at 40 psi and 6484 to 8704 cP at 80 psi whereas Comp Ex C15-C17 range from 9241 to 14160 cP at 40 psi and 10768 to 16616 cP at 80 psi. The Severs viscosity stability is an important indicator of performance in high shear processes such as knife coating.

TABLE 11

Fusion Time and Shore A Hardness for
Ex 16-17 and Comp Ex C15-C17.

| Ex | Viscosity Additive | Fusion Time (Min) | Shore A Hardness |
|---|---|---|---|
| 16 | 6 | 16.97 | 67 |
| 17 | 7 | 19.20 | 69 |
| C15 | C4 | 19.90 | 72 |
| C16 | C5 | 19.67 | 74 |
| C17 | VA1 | 18.43 | 70 |

The plastisol of Ex 16 comprising the glycol ether benzoate of Ex 6, showed a particularly faster fusion time (16.97 min) than the plastisols comprising non-oxygenated alkyl monobenzoates and isodecyl benzoate, Comp Ex C15-C17, ranging from 18.43 to 19.9 min. Reduced fusion time can enable faster production rates and lower energy use for manufacturers of articles from PVC plastisols. The glycol ether benzoates of Ex 6 and 7 are more efficient plasticizers than non-oxygenated alkyl monobenzoates and isodecyl benzoate as shown by the lower Shore A Hardness values for Ex 16 and 17 plastisols (67-69) as compared to the Shore A Hardness values of Comp Ex C15-C17 (70-74). Higher efficiency means that less plasticizer can be used to attain desired product properties, often resulting in cost savings to the manufacturer.

Ex 18-20 and Comp Ex C18-C19—Plasticizer Performance

An experiment was conducted to assess the relative performance of glycol ether benzoates based on ethoxylated 2-ethylhexanol against isodecyl benzoate and isotridecyl benzoate as plastisol viscosity control additives. These plastisol formulations consisted of 100 phr Geon 121A PVC resin, 3 phr epoxidized soybean oil, 3 phr AKCROSTAB LT 4798 stabilizer, 45 phr DOTP, and 15 phr of the viscosity control additive. The viscosity control additive used for each example is identified in Tables 12-14 by the Example number or Comparative Example number for those produced and by the VA# above for those purchased. The PVC resin, epoxidized soybean oil, AKCROSTAB LT 4798, DOTP, and viscosity control additive levels are used in all subsequent plastisol formulations. Brookfield Viscosities were measured at 2 rpm and 20 rpm. Severs viscosities were measured at 40 psi and 80 psi. Both viscosity measurements were performed on the day the plastisol was made (initial) and then again at first, third, and seventh days after production and are listed in Table 12 and 13, respectively. Fusion time for each plastisol and Shore A hardness were measured and are listed in Table 14.

TABLE 12

Plastisol Brookfield viscosity for Ex 18-20 and Comp. Ex C18-C19.

| Ex | Viscosity Additive | rpm | Initial | Day 1 | Day 3 | Day 7 |
|---|---|---|---|---|---|---|
| | | | Viscosity (cP) | | | |
| 18 | 8 | 2 | 5150 | 3920 | 4000 | 4080 |
| 19 | 9 | 2 | 4400 | 4240 | 4340 | 4400 |
| 20 | 10 | 2 | 2900 | 2920 | 3160 | 3200 |
| C18 | C6 | 2 | 3200 | 3240 | 3300 | 3440 |
| C19 | VA1 | 2 | 3350 | 3940 | 3820 | 3460 |
| 18 | 8 | 20 | 2920 | 2990 | 3090 | 3150 |
| 19 | 9 | 20 | 2980 | 3230 | 3310 | 3450 |
| 20 | 10 | 20 | 2420 | 2560 | 2660 | 2770 |
| C18 | C6 | 20 | 2640 | 2870 | 2930 | 3100 |
| C19 | VA1 | 20 | 2660 | 2980 | 2950 | 3120 |

TABLE 13

Plastisol Severs viscosity-Ex 18-20 and Comp Ex C18-C19

| Ex | Viscosity Additive | Psi | Initial | Day 1 | Day 3 | Day 7 |
|---|---|---|---|---|---|---|
| | | | Viscosity (cP) | | | |
| 18 | 8 | 40 | 11222 | 11434 | 10583 | 10954 |
| 19 | 9 | 40 | 13211 | 12207 | 10595 | 11762 |
| 20 | 10 | 40 | 11429 | 11390 | 9690 | 10780 |
| C18 | C6 | 40 | 16999 | 16431 | 13469 | 15469 |
| C19 | VA1 | 40 | 12696 | 11874 | 10171 | 10854 |
| 18 | 8 | 80 | 12695 | 12731 | 11886 | 12053 |
| 19 | 9 | 80 | 14095 | 13745 | 11822 | 12865 |
| 20 | 10 | 80 | 13448 | 12962 | 11192 | 11858 |
| C18 | C6 | 80 | 19635 | 18150 | 14596 | 15549 |
| C19 | VA1 | 80 | 14181 | 13435 | 11126 | 12215 |

Although the ethoxylated 2-ethylhexyl benzoates are not as advantaged in plastisol viscosity control as other glycol ether benzoates, they outperform isotridecyl benzoate in the higher shear Severs viscosity, and the plastisol of Example 18 comprising the glycol ether benzoate of Example 10 outperforms isotridecyl benzoate at all conditions tested in both Brookfield and Severs viscosity. Each of the ethoxylated 2-ethylhexyl benzoates is higher molecular weight than isodecyl benzoate, translating into lower emissions during manufacture and processing of the plastisols.

TABLE 14

Fusion Time and Shore A Hardness for Ex 18-20 and Comp Ex C18-C19.

| Ex | Viscosity Additive | Fusion Time (Min) | Shore A Hardness |
|---|---|---|---|
| 18 | 8 | 20.23 | 70 |
| 19 | 9 | 19.90 | 71 |
| 20 | 10 | 19.80 | 71 |
| C18 | C6 | 19.27 | 72 |
| C19 | VA1 | 18.97 | 71 |

Ex 21 and Comp Ex C20

An experiment was conducted to compare the performance of glycol ether benzoates as components of a PVC plastisol formulation to a control formulation containing only a general-purpose plasticizer, DOTP (VA4). These plastisol formulations consisted of 100 phr Geon 121A PVC resin, 3 phr epoxidized soybean oil, 3 phr AKCROSTAB LT 4798 stabilizer, 45 phr DOTP, and 15 phr of the viscosity control additive, except that the control formulation Comp Ex C20 consisted of 60 phr DOTP (the viscosity control additive in this example was the general-purpose plasticizer). The viscosity control additive used for each example is identified in Tables 15-17 by the Example number or Comparative Example number for those produced and by the VA# above for those purchased. The PVC resin, epoxidized soybean oil, AKCROSTAB LT 4798, DOTP, and viscosity control additive levels are used in all subsequent plastisol formulations. Brookfield Viscosities were measured at 2 rpm and 20 rpm. Severs viscosities were measured at 40 psi and 80 psi. Both viscosity measurements were performed on the day the plastisol was made (initial) and then again at first, third, and fourteenth days after production and are listed in Table 15 and 16, respectively. Fusion time for each plastisol was measured and results are listed in Table 17.

TABLE 15

Plastisol Brookfield viscosity for Ex 21-22 and Comp Ex C20.

| Ex | Viscosity Additive | rpm | Initial | Day 1 | Day 3 | Day 14 |
|---|---|---|---|---|---|---|
| | | | | Viscosity (cP) | | |
| C20 | VA4 | 2 | 3840 | 5080 | 5350 | 7780 |
| 21 | 5 | 2 | 2260 | 2860 | 3320 | 4060 |
| 22 | 7 | 2 | 2500 | 2940 | 3580 | 4700 |
| C20 | VA4 | 20 | 3560 | 4345 | 4480 | 5230 |
| 21 | 5 | 20 | 1815 | 2435 | 2800 | 2980 |
| 22 | 7 | 20 | 2045 | 2355 | 2790 | 3455 |

TABLE 16

Plastisol Severs viscosity for Ex 21-22 and Comp Ex C20.

| Ex | Viscosity Additive | psi | Initial | Day 1 | Day 3 | Day 14 |
|---|---|---|---|---|---|---|
| | | | | Viscosity (cP) | | |
| C20 | VA4 | 40 | 20104 | 21317 | 22262 | 17392 |
| 21 | 5 | 40 | 6207 | 6650 | 6693 | 7079 |
| 22 | 7 | 40 | 10736 | 12684 | 12600 | 12997 |
| C20 | VA4 | 80 | 22446 | 23511 | 23623 | 18514 |
| 21 | 5 | 80 | 6891 | 7309 | 7433 | 8184 |
| 22 | 7 | 80 | 16054 | 18359 | 18507 | 19509 |

The viscosity data illustrate superior plastisol viscosity reduction and control for plastisols comprising the glycol ether benzoates, compared to that obtained with the general-purpose DOTP alone, Comp Ex C20. Ex 21 has much lower Brookfield and Severs viscosity values at each measurement time and condition compared to Comp Ex C20. Ex 22 has much lower Brookfield viscosity values at each measurement time and condition compared to Comp Ex C20, and lower Severs viscosity values at each time and condition except at the 14-day time at 80 psi. Particularly unexpected was the ability of the glycol ether benzoates, comprising only 25% of the plasticizer component content, to confer reductions of the Brookfield viscosity of up to almost 50% and reductions of the Severs viscosity of up to almost 70% compared to that obtained with the general-purpose DOTP alone.

TABLE 17

Fusion Time for Ex 21-22 and Comp Ex C20.

| Ex | Viscosity Additive | Fusion Time (Min) |
|---|---|---|
| C20 | VA4 | 19.17 |
| 21 | 5 | 17.80 |
| 22 | 7 | 15.90 |

Each of the plastisols comprising glycol ether benzoates, Ex 21 and 22, showed faster fusion times than the plastisol comprising the general-purpose DOTP alone, Comp Ex C20. Reduced fusion time can enable faster production rates and lower energy use for manufacturers of articles from PVC plastisols. The unexpected reduction in the fusion time distinguishes the present invention from additives that are effective in plastisol viscosity reduction but do not contribute to or are detrimental to plasticization, and those which can speed fusion but increase plastisol viscosity.

Comp Ex C21-C25—Plasticizer Performance

An experiment was conducted to assess the relative performance of aliphatic glycol ether esters as plastisol viscosity control additives. These plastisol formulations consisted of 100 phr Geon 121A PVC resin, 3 phr epoxidized soybean oil, 3 phr AKCROSTAB LT 4798 stabilizer, 45 phr DOTP, and 15 phr of the viscosity control additive. The PVC resin, epoxidized soybean oil, AKCROSTAB LT 4798, DOTP, and viscosity control additive levels are used in all subsequent plastisol formulations. Brookfield Viscosities were measured at 2 rpm and 20 rpm. Severs viscosities were measured at 40 psi and 80 psi. Both viscosity measurements were performed on the day the plastisol was made (initial) and then again at first and seventh days after production and are listed in Table 18 and 19, respectively.

Fusion time for each plastisol and Shore A hardness were measured and are listed in Table 20.

TABLE 18

Plastisol Brookfield viscosity for Comp Ex C21-C25.

| Ex | Viscosity Additive | rpm | Initial | Day 1 | Day 7 |
|---|---|---|---|---|---|
| | | | | Viscosity (cP) | |
| C21 | C7 | 2 | 1360 | 1400 | 1420 |
| C22 | C8 | 2 | 1640 | 1720 | 2020 |
| C23 | C9 | 2 | 1340 | 1320 | 1620 |
| C24 | VA1 | 2 | 1800 | 1800 | 2000 |
| C25 | VA2 | 2 | 1800 | 1800 | 1940 |
| C21 | C7 | 20 | 1210 | 1230 | 1270 |
| C22 | C8 | 20 | 1460 | 1470 | 1900 |
| C23 | C9 | 20 | 1210 | 1230 | 1530 |
| C24 | VA1 | 20 | 1710 | 1760 | 2010 |
| C25 | VA2 | 20 | 1770 | 1770 | 1970 |

TABLE 19

Plastisol Severs viscosity for Comp Ex C21-C25.

| Ex | Viscosity Additive | psi | Initial | Day 1 | Day 7 |
|---|---|---|---|---|---|
| | | | | Viscosity (cP) | |
| C21 | C7 | 40 | 12066 | 13130 | 11906 |
| C22 | C8 | 40 | 13006 | 12742 | 12208 |
| C23 | C9 | 40 | 11719 | 11374 | 11115 |
| C24 | VA1 | 40 | 11880 | 11256 | 9981 |
| C25 | VA2 | 40 | 12350 | 11951 | 10639 |
| C21 | C7 | 80 | 13304 | 14086 | 12594 |
| C22 | C8 | 80 | 14011 | 13903 | 13025 |
| C23 | C9 | 80 | 12391 | 12038 | 11191 |
| C24 | VA1 | 80 | 14259 | 13438 | 11544 |
| C25 | VA2 | 80 | 14574 | 13835 | 12133 |

TABLE 20

Fusion Time and Shore A Hardness for Comp Ex C21-C25.

| Ex | Viscosity Additive | Fusion Time (Min) | Shore A Hardness |
|---|---|---|---|
| C21 | C7 | 20.57 | 73 |
| C22 | C8 | 21.10 | 74 |
| C23 | C9 | 20.87 | 74 |
| C24 | VA1 | 18.77 | 71 |
| C25 | VA2 | 20.50 | 70 |

Although good viscosity control was exhibited by the 2-ethylhexanoate esters, (as seen in Comp Ex C21-C23) they are deficient in fusion rates and plasticizing efficiency as measured by Shore A hardness compared to the inventive examples and to isodecyl benzoate, VA1 (C24). Triethylene glycol di-2-ethylhexanoate, VA2 (C25), does show a combination of good plasticizing efficiency and good viscosity control.

Glycol ether-based benzoate esters may also be used as a component of fast-fusing plasticizer blends. Fast-fusing plasticizers are highly solvating towards PVC, with a strong plasticizing effect providing good efficiency while speeding fusion rates. These desirable properties can be accompanied by increased plastisol viscosities, and viscosity buildup over time.

An experiment was conducted to assess the relative performance of 2-butoxyethyl benzoate (Ex 1) as a component of fast fusing plasticizer blends compared to other fast-fusing plasticizers in PVC plastisols. These plastisol formulations consisted of 100 phr Geon 121A PVC resin, 3 phr epoxidized soybean oil, 3 phr AkcrostabTM LT 4798 stabilizer, 42 phr DOTP, and 18 phr of a fast-fusing plasticizer component. The fast-fusing plasticizer component is identified in Table 21. Composition FF-C1 comprises dipropylene glycol dibenzoate, a common and well-known fast-fusing plasticizer for PVC.

TABLE 21

Compositions in Fast-Fusing Plasticizer Experiment

| Ex | Description of Fast-Fusing Component |
|---|---|
| FF-1 | 2:1 Diethylene glycol dibenzoate: 2-Butoxyethyl benzoate |
| FF-2 | 1:1 Diethylene glycol dibenzoate: 2-Butoxyethyl benzoate |
| FF-3 | 1:1 Dibutyl terephthalate: 2-Butoxyethyl benzoate |
| FF-C1 | Dipropylene glycol dibenzoate |
| FF-C3 | Di-4-methyl-2-pentyl terephthalate |

Brookfield viscosities were measured at 2 rpm and 20 rpm on the day the plastisols were made (initial), and then again on the first, third, and seventh days after production and are listed in Table 22.

TABLE 22

Plastisol Brookfield Viscosities from Fast-Fusing Plasticizer Experiment.

| Ex | rpm | Initial | Day 1 | Day 3 | Day 7 |
|---|---|---|---|---|---|
| | | | Viscosity (cP) | | |
| FF-1 | 2 | 1820 | 2840 | 3620 | 3600 |
| FF-2 | 2 | 2140 | 2580 | 3340 | 3340 |
| FF-3 | 2 | 2660 | 2220 | 3000 | 2960 |
| FF-C1 | 2 | 3900 | 3820 | 5200 | 4600 |
| FF-C2 | 2 | 2580 | 2900 | 3400 | 3580 |
| FF-C3 | 2 | 3220 | 3540 | 4280 | 4080 |
| FF-1 | 20 | 1704 | 2400 | 2960 | 2845 |
| FF-2 | 20 | 1880 | 2070 | 2660 | 2450 |
| FF-3 | 20 | 2225 | 1800 | 2270 | 2190 |
| FF-C1 | 20 | 3605 | 3655 | 4705 | 4245 |
| FF-C3 | 20 | 3265 | 3545 | 4510 | 3985 |

The fusion behavior and plasticizer efficiency, as measured by Shore A Hardness, are shown in Table 23.

TABLE 23

Fusion Times and Shore A Hardnesses from Fast-Fusing Plasticizer Experiment.

| Ex | Fusion Time (min) | Shore A Hardness |
|---|---|---|
| FF-1 | 15.40 | 72 |
| FF-2 | 13.17 | 72 |
| FF-3 | 16.23 | 72 |
| FF-C1 | 16.40 | 73 |
| FF-C3 | 17.90 | 75 |

The glycol ether-based plasticizer component in fast-fuser Inventive Ex FF-1, FF-2, and FF-3 provided a significant reduction in plastisol Brookfield viscosity when compared to Comp Ex FF-C1. Inventive Ex FF-1 and FF-2 comprise diethylene glycol dibenzoate, very similar structurally to the dipropylene glycol dibenzoate which comprises Comp Ex FF-C1, yet the plastisols of Ex FF-1 and FF-2 show much lower plastisol viscosity than in Comp Ex FF-C1. Ex FF-3 illustrates that the low viscosity can also be conferred to a fast-fusing terephthalate plasticizer blend. Table 23 shows that the Inventive Examples are also advantaged in the efficiency parameters of fusion time and Shore A hardness.

EVALUATION OF DRY BLENDS

Ex 23-31 and Comp Ex C26-C28

Selected examples of the glycol ether benzoates were used in dry blend formulations. The dry blend formulations consisted of OxyVinyls 240F PVC resin (OxyVinyls, LP), K-value 70, along with 18 phr Burgess 30P clay (Burgess Pigment Company) and 5 phr epoxidized soybean oil (Drapex 6.8, Galata Chemicals) were used and mixtures of 60 phr DOTP and 10 phr of the additive, except that Comp Ex C28 used 70 phr DOTP only. Dry times were measured in accordance with ASTM Method D2396, "Standard Test Methods for Powder-Mix Time of PVC Resins Using a Torque Rheometer." The dry times, the times for the plasticized PVC formulation to form a free-flowing blend, are reported in Table 24.

TABLE 24

Dry times of Ex 23-31 and Comp Ex C26-C28.

| Ex # | Plasticizer | Dry Time (Min) |
| --- | --- | --- |
| 23 | 1 | 3.37 |
| 24 | 2 | 1.93 |
| 25 | 3 | 1.73 |
| 26 | 4 | 2.23 |
| 27 | 5 | 2.67 |
| 28 | 6 | 2.60 |
| 29 | 7 | 2.50 |
| 30 | 8 | 2.93 |
| 31 | 9 | 2.70 |
| C26 | VA1 | 3.13 |
| C27 | VA3 | 3.33 |
| C28 | VA4 | 4.00 |

The dry time data shows clear reductions in the time required to dry when glycol ether benzoates are incorporated into PVC dry blend formulations. Each glycol ether benzoate reduces the dry time compared to when no different plasticizer is used, Comp Ex C28. With the exception of the plastisol of Ex 23 which was made using 2-butoxyethyl benzoate, Ex 1, each glycol ether benzoate is more efficient at reducing dry time than the compounds in VA1, VA3, and VA4. Faster dry time can provide economic benefit to producers of dry blends from higher throughput and increased capacity utilization, and improved flexibility in their manufacturing operations.

EVALUATION OF EMISSIONS

Emissions testing was conducted according to the German AgBB (Committee for Health-Related Evaluation of Building Products) methodology, February 2015 regulations. Fused sheet samples were prepared from plastisols containing 100 phr Geon 121A, 24 phr EASTMAN 168 Non-Phthalate Plasticizer, 15 phr DBT, 3 phr epoxidized soybean oil, 3 phr AKCROSTAB LT 4798 stabilizer, and 5 phr additional plasticizer as described in Table 25.

Emission analysis utilized Markes Microchambers in conjunction with automated thermal desorption gas chromatography and mass spectrometry for detection. Suitably sized discs were cut from the samples and placed in the Microchamber tests cells. The cells were maintained at 23° C. and dried air was used to sweep the test cell at approximately 20.5 mL/min. Emissions were collected after 3 and 28 days using Tenax TA thermal desorption tubes. Emissions data were evaluated using the AgBB methodology, calculated as indoor air concentrations in micrograms/cubic meter ($\mu g/m^3$) using toluene equivalents. Total volatile organic compound (TVOC) and total semi-volatile organic compound (TSVOC) concentrations were determined as the sum of all components of concentration greater than or equal to 5 $pg/m^3$. Compounds eluting between C6 (hexane) and C16 (hexadecane) are assigned as VOC, and compounds eluting between C16 and C22 (docosane) are assigned as SVOC. According to the AgBB protocol, TVOC emissions after 3 days must not exceed 10 $mg/m^3$, and after 28 days must not exceed 1 $mg/m^3$. TSVOC emissions after 28 days must not exceed 0.1 $mg/m^3$.

TABLE 25

TVOC and TSVOC emissions for Ex 32 and Comp Ex C29-C32, mg/m3.

| Ex | Additional Plasticizer | TVOC 3 days | TVOC 28 days | TSVOC 28 Days |
| --- | --- | --- | --- | --- |
| 32 | 7 | 1.44 | 0.58 | <0.01 |
| C29 | VA1 | 1.38 | 0.48 | 0.04 |
| C30 | VA2 | 1.66 | 0.65 | <0.01 |
| C31 | VA5 | 1.79 | 0.72 | <0.01 |
| C33 | VA6 | 1.95 | 0.67 | 0.04 |

All samples passed the AgBB emissions testing. However, JayFlex MB10, VA1, clearly contributed to SVOC emissions as did the mixture of hydrocarbons in the HB-40 Process Fluid, VA6. Of the 0.04243 $mg/m^3$ emissions in Comparative Example C29, 0.03541 $mg/m^3$ were from the isodecyl benzoate itself. Contributions to SVOC emissions greater than 0.01 $mg/m^3$ were not observed with 2-(2-(2-butoxyethoxy)ethoxy)ethyl benzoate, Ex 32, or TEG-EH and DOA, Comp Ex C30 and C31. Species which contribute to SVOC emissions may cause articles such as flooring and wall covering to fail emissions testing should standards tighten, which has occurred in the past and may in the future as desires for improved indoor air quality have heightened.

Other embodiments will be apparent to those skilled in the art from consideration of the specification and practice of the embodiments disclosed herein. It will be understood that variations and modifications can be effected within the spirit and scope of the disclosed embodiments. It is further intended that the specification and examples be considered as exemplary only, with a true scope and spirit of the disclosed embodiments being indicated by the following claims.

We claim:

1. A plasticizer composition comprising:
   (a) a general-purpose plasticizer; and
   (b) a plasticizer of formula I:

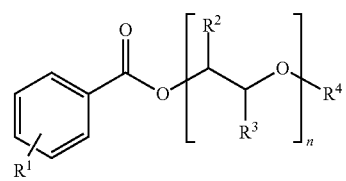

wherein:
R¹ is hydrogen or methyl;
R² and R³ are independently hydrogen or methyl, with the proviso that R² and R³ are not each methyl;
R⁴ is unbranched or branched ($C_{1-10}$) alkyl or phenyl; and
n is an integer from 1 to 8;
wherein the plasticizer of formula I is present in the plasticizer composition from about 10 wt. % to about 50 wt. % based on the total weight of general-purpose plasticizer and plasticizer of formula I; and wherein the plasticizer composition further comprises: (c) a fast-fusing plasticizer comprising:
(i) dibenzoate plasticizer or
(ii) a plasticizer of formula II:

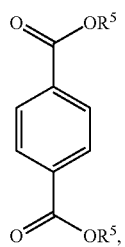

wherein each R⁵ is —O—CH₂—CH₂—O—($C_{1-9}$) alkyl.

2. The plasticizer composition of claim 1, wherein R⁴ is methyl, ethyl, unbranched or branched propyl, unbranched or branched butyl, unbranched or branched hexyl, unbranched or branched octyl, or phenyl.

3. The plasticizer composition of claim 1, wherein the plasticizer of formula I is 2-methoxyethyl benzoate, 2-ethoxyethyl benzoate, 2-propoxyethyl benzoate, 2-butoxyethyl benzoate, 2-hexyloxyethyl benzoate, 2-(2-ethylhexyloxy)ethyl benzoate, 2-phenoxyethyl benzoate, 2-(2-methoxyethoxy) ethyl benzoate, 2-(2-ethoxyethoxy)ethyl benzoate, 2-(2-propoxyethoxy)ethyl benzoate, 2-(2-butoxyethoxy)ethyl benzoate, 2-(2-hexyloxyethoxy)ethyl benzoate, 2-(2-(2-ethylhexyloxy)ethoxy)ethyl benzoate, 2-(2-phenoxyethoxy)ethyl benzoate, 2-(2-(2-methoxyethoxy)ethoxy)ethyl benzoate, 2-(2-(2-ethoxyethoxy)ethoxy)ethyl benzoate, 2-(2-(2-propoxyethoxy)ethoxy)ethyl benzoate, 2-(2-(2-butoxyethoxy)ethoxy) ethyl benzoate, 2-(2-(2-hexyloxyethoxy)ethoxy)ethyl benzoate, 2-(2-(2-ethylhexyloxy)ethoxy)ethoxy)ethyl benzoate, 2-(2-(2-phenoxyethoxy)ethoxy) ethyl benzoate, 1-methoxy-2-propyl benzoate, 1-ethoxy-2-propyl benzoate, 1-propoxy-2-propyl benzoate, 1-butoxy-2-propyl benzoate, 1-phenoxy-2-propyl benzoate, 2-methoxy-1-propyl benzoate, 2-ethoxy-1-propyl benzoate, 2-propoxy-1-propyl benzoate, 2-butoxy-1-propyl benzoate, 2-phenoxy-1-propyl benzoate, isomers of dipropylene glycol monomethyl ether benzoate, isomers of dipropylene glycol monoethyl ether benzoate, isomers of dipropylene glycol monopropyl ether benzoate, isomers of dipropylene glycol monobutyl ether benzoate, isomers of tripropylene glycol monomethyl ether benzoate, isomers of tripropylene glycol monoethyl ether benzoate, isomers of tripropylene glycol monopropyl ether benzoate, or isomers of tripropylene glycol monobutyl ether benzoate.

4. The plasticizer composition of claim 1, wherein the general-purpose plasticizer is a terephthalate ester plasticizer, a phthalate ester plasticizer, a cyclohexane-1,2-dicarboxylate ester plasticizer, a cyclohexane-1,4-dicarboxylate ester plasticizer, an alkyl sulfonate plasticizer, a pentaerythritol ester plasticizer, or a citrate ester plasticizer.

5. The plasticizer composition of claim 1, wherein the general-purpose plasticizer is bis(2-ethylhexyl) terephthalate, bis(isononyl) cyclohexane-1,2-dicarboxylate, or bis(isononyl) phthalate.

6. The plasticizer composition of claim 1, wherein the dibenzoate plasticizer comprises oxybis(ethane-2,1-diyl) dibenzoate, (ethane-1,2-diylbis(oxy))bis(ethane-2,1-diyl) dibenzoate, polyethylene glycol dibenzoate, propane-1,3-diyl dibenzoate, oxybis(propane-3,1-diyl) dibenzoate, (propane-1,3-diylbis(oxy))bis(propane-3,1-diyl) dibenzoate, 2,2,4-trimethyl-1,3-pentanediol dibenzoate, or combinations thereof.

7. The plasticizer composition of claim 1, wherein the ($C_{1-9}$) alkyl in each R⁵ is independently chosen from methyl, ethyl, unbranched or branched propyl, unbranched or branched butyl, unbranched or branched pentyl, or unbranched or branched hexyl.

8. A plastisol comprising
(a) a resin;
(b) a general-purpose plasticizer; and
(c) a plasticizer of formula I:

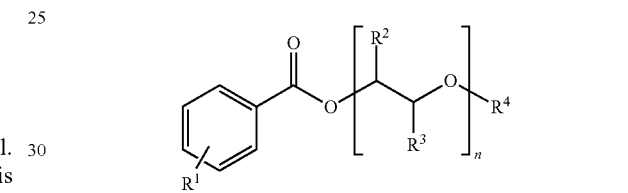

wherein:
R¹ is hydrogen or methyl;
R² and R³ are independently hydrogen or methyl, with the proviso that R²; and R³ are not each methyl;
R⁴ is unbranched or branched ($C_{1-10}$) alkyl or phenyl; and
n is an integer from 1 to 8;
wherein the plastisol comprises 30 to 200 parts plasticizer component per 100 parts resin, wherein the plasticizer component comprises the general-purpose plasticizer and the plasticizer of formula I; and wherein the plasticizer component comprises 10 wt. % to 50 wt. % of the plasticizer of formula I, wherein the plastisol further comprises: (d) a fast-fusing plasticizer wherein the fast-fusing plasticizer comprises:
(i) dibenzoate plasticizer, or
(ii) a plasticizer of formula II:

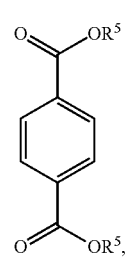

wherein: each R⁵ is —O—CH₂—CH₂—O—($C_{1-9}$) alkyl.

9. The plastisol of claim 8, wherein R⁴ is methyl, ethyl, unbranched or branched propyl, unbranched or branched butyl, unbranched or branched hexyl, unbranched or branched octyl, or phenyl.

10. The plastisol of claim 8, wherein the resin comprises polyvinyl chloride, polyvinyl acetate, acrylic polymers, and/or vinyl chloride-containing copolymers.

11. The plastisol of claim 8, wherein the plasticizer of formula I is 2-methoxyethyl benzoate, 2-ethoxyethyl benzoate, 2-propoxyethyl benzoate, 2-butoxyethyl benzoate, 2-hexyloxyethyl benzoate, 2-(2-ethylhexyloxy) ethyl benzoate, 2-phenoxyethyl benzoate, 2-(2-methoxyethoxy)ethyl benzoate, 2-(2-ethoxyethoxy)ethyl benzoate, 2-(2-propoxyethoxy)ethyl benzoate, 2-(2-butoxyethoxy)ethyl benzoate, 2-(2-hexyloxyethoxy)ethyl benzoate, 2-(2-(2-ethylhexyloxy)ethoxy)ethyl benzoate, 2-(2-phenoxyethoxy)ethyl benzoate, 2-(2-(2-methoxyethoxy)ethoxy)ethyl benzoate, 2-(2-(2-ethoxyethoxy)ethoxy)ethyl benzoate, 2-(2-(2-propoxyethoxy)ethoxy)ethyl benzoate, 2-(2-(2-butoxyethoxy)ethoxy) ethyl benzoate, 2-(2-(2-hexyloxyethoxy)ethoxy)ethyl benzoate, 2-(2-(2-ethylhexyloxy)ethoxy)ethoxy)ethyl benzoate, 2-(2-(2-phenoxyethoxy)ethoxy) ethyl benzoate, 1-methoxy-2-propyl benzoate, 1-ethoxy-2-propyl benzoate, 1-propoxy-2-propyl benzoate, 1-butoxy-2-propyl benzoate, 1-phenoxy-2-propyl benzoate, 2-methoxy-1-propyl benzoate, 2-ethoxy-1-propyl benzoate, 2-propoxy-1-propyl benzoate, 2-butoxy-1-propyl benzoate, 2-phenoxy-1-propyl benzoate, isomers of dipropylene glycol monomethyl ether benzoate, isomers of dipropylene glycol monoethyl ether benzoate, isomers of dipropylene glycol monopropyl ether benzoate, isomers of dipropylene glycol monobutyl ether benzoate, isomers of tripropylene glycol monomethyl ether benzoate, isomers of tripropylene glycol monoethyl ether benzoate, isomers of tripropylene glycol monopropyl ether benzoate, or isomers of tripropylene glycol monobutyl ether benzoate.

12. The plastisol of claim 8, wherein the general-purpose plasticizer is a terephthalate ester plasticizer, a phthalate ester plasticizer, a cyclohexane-1,2-dicarboxylate ester plasticizer, a cyclohexane-1,4-dicarboxylate ester plasticizer, an alkyl sulfonate plasticizer, a pentaerythritol ester plasticizer, or a citrate ester plasticizer.

13. The plastisol of claim 8, wherein the general-purpose plasticizer is bis(2-ethylhexyl) terephthalate, bis(isononyl) cyclohexane-1,2-dicarboxylate, or bis(isononyl) phthalate.

14. The plastisol of claim 8, wherein the dibenzoate plasticizer comprises oxybis(ethane-2,1-diyl) dibenzoate, (ethane-1,2-diylbis(oxy))bis(ethane-2,1-diyl) dibenzoate, polyethylene glycol dibenzoate, propane-1,3-diyl dibenzoate, oxybis(propane-3,1-diyl)dibenzoate, (propane-1,3-diyl-bis(oxy))bis(propane-3,1-diyl) dibenzoate, 2,2,4-trimethyl-1,3-pentanediol dibenzoate, or combinations thereof.

15. The plastisol of claim 8, wherein the ($C_{1-9}$) alkyl in each $R^5$ is independently chosen from methyl, ethyl, unbranched or branched propyl, unbranched or branched butyl, unbranched or branched pentyl, or unbranched or branched hexyl.

16. The plastisol of claim 8, wherein the plastisol comprises 30 to 150 parts plasticizer component per 100 parts resin and wherein the plasticizer component comprises 10 wt. % to 40 wt. % of the plasticizer of formula I.

17. The plastisol of claim 8 whereby a fused sheet formed from the plastisol has a total semi-volatile organic compound emissions (TSVOC) of less than 0.01 mg/m³ using toluene equivalents after 28 days as evaluated using an AgBB methodology.

* * * * *